United States Patent
Hsu et al.

(10) Patent No.: US 8,273,903 B2
(45) Date of Patent: Sep. 25, 2012

(54) METHOD FOR PREPARING THE CITRACONIC ANHYDRIDE AND METHOD FOR ISOMERIZING/DEHYDRATING ITACONIC ACID

(75) Inventors: Hsi-Yen Hsu, Taipei (TW); Yu-Shan Chao, HsinChu (TW)

(73) Assignee: Industrial Technology Research Institute, Hsinchu County (TW)

( * ) Notice: Subject to any disclaimer, the term of this patent is extended or adjusted under 35 U.S.C. 154(b) by 127 days.

(21) Appl. No.: 12/981,813

(22) Filed: Dec. 30, 2010

(65) Prior Publication Data

US 2011/0160466 A1    Jun. 30, 2011

(30) Foreign Application Priority Data

Dec. 30, 2009 (TW) ................................ 98145759 A

(51) Int. Cl.
    *C07D 307/60* (2006.01)
(52) U.S. Cl. ........................................................ 549/261
(58) Field of Classification Search .................... 549/261
    See application file for complete search history.

(56) References Cited

U.S. PATENT DOCUMENTS

| | | | |
|---|---|---|---|
| 2,966,498 A | 12/1960 | Humphrey |
| 5,329,022 A | 7/1994 | Talma et al. |
| 5,670,659 A | 9/1997 | Alas et al. |
| 5,824,820 A | 10/1998 | Alas |

FOREIGN PATENT DOCUMENTS

| | | |
|---|---|---|
| CA | 2059449 C | 7/2003 |
| CN | 1110676 A | 10/1995 |
| CN | 1150584 A | 5/1997 |
| CN | 1066432 C | 5/2001 |
| CN | 1077563 C | 1/2002 |
| EP | 0495544 A1 | 7/1992 |
| EP | 0665211 A1 | 8/1995 |
| EP | 0749952 A1 | 12/1996 |
| GB | 1246349 | 9/1971 |
| JP | 04312571 A | 11/1992 |
| JP | 09117296 A | 5/1997 |
| JP | 09132572 A | 5/1997 |
| RU | 2058296 C1 | 4/1996 |
| WO | 94/21589 A1 | 9/1994 |
| WO | 95/06026 A1 | 3/1995 |

OTHER PUBLICATIONS

Examination opinion issued by the Taiwan Intellectual Property Office on May 21, 2012, for the above-referenced application's counterpart application in Taiwan (Application No. 098145759 filed Dec. 30, 2009).

*Primary Examiner* — Bernard Dentz
(74) *Attorney, Agent, or Firm* — Pai Patent & Trademark Law Firm; Chao-Chang David Pai

(57) ABSTRACT

The disclosure provides a method for preparing the citraconic anhydride and a method for isomerizing/dehydrating itaconic acid. The method for preparing the citraconic anhydride includes the following steps: providing itaconic acid as a starting material; and subjecting the itaconic acid to an isomerization/dehydration reaction in the presence of a catalyst to obtain the citraconic anhydride, wherein the catalyst includes a heteropolyacid or heteropolyacid salt.

19 Claims, No Drawings

METHOD FOR PREPARING THE CITRACONIC ANHYDRIDE AND METHOD FOR ISOMERIZING/DEHYDRATING ITACONIC ACID

CROSS REFERENCE TO RELATED APPLICATIONS

This application is based upon and claims the benefit of priority from the prior Taiwan Patent Application No. 098145759, filed on Dec. 30, 2009, the entire contents of which are incorporated herein by reference.

BACKGROUND OF THE INVENTION

1. Field of the Invention

The present invention relates to a method for preparing the citraconic anhydride, and in particular relates to a method for preparing the citraconic anhydride from itaconic acid.

2. Description of the Related Art

Citraconic anhydride (also known as 2-methyl maleic anhydride) is a derivate of maleic anhydride. Citraconic anhydride is a product which has seen increasing demand by different industries. For example, citraconic anhydride can serve as an additive to improve the properties of unsaturated polyester resin or the raw material for preparing a diol compound via hydrogenation.

It is known in the art that citraconic anhydride can be prepared by pyrolysis and dehydration of citric acid (or a carboxylic acid containing six carbon atoms). In recent years, due to rapid advances in fermentation technology, itaconic acid can be conveniently prepared by microbiological fermentation of carbohydrates, such as glucose or glycerol. The obtained itaconic acid can serve as a raw material for preparing the citraconic anhydride via a dehydration/isomerization reaction.

In order to improve reaction yields, a catalyst in order to accelerate the isomerization reaction has been proposed. Thus, for example, U.S. Pat. No. 2,966,498 describes the manufacturing of citraconic anhydride from itaconic acid, using a catalyst based on alkali metal sulphate and dihydrogenophosphate.

U.S. Pat. No. 5,329,022 describes the manufacturing of citraconic anhydride from itaconic acid, using a catalyst based on amine or phosphine. The reaction additionally needs to employ xylene as a solvent and acetic anhydride to dehydrate water. An additional purification step is required, however, for removing the undesired acetic acid side product.

U.S. Pat. Nos. 5,670,659 and 5,824,820 describe the manufacturing of citraconic anhydride from itaconic acid in the presence of a catalyst, based on organic amine or organic acid salt, and an entrainer. However, since the organic catalyst is apt to react with itaconic acid to form oligomers, the reaction provides poor citraconic anhydride yields and it is difficult to separate the catalyst from the residual reaction solution.

WO No. 1995006026 describes the manufacturing of citraconic anhydride from itaconic acid in the presence of organic acids with sulfonic acid groups as a catalyst and a solvent as an entrainer. The organic acid catalyst, however, is apt to react with itaconic acid, resulting in low yields of less than 50%, and the organic acid catalyst is nonrecyclable.

WO 1994021589 describes the manufacturing of citraconic anhydride from itaconic acid in the presence of organic amide as a catalyst. The citraconic anhydride yield is less than 75%, and the organic amide catalyst is nonrecyclable.

Therefore, it is necessary to develop a novel method for preparing the citraconic anhydride from itaconic acid with high yields. Accordingly, the disclosure is the provision of a process, for the preparation of citraconic anhydride, with high yield, from itaconic acid in the presence of a heteropolyacid or heteropolyacid salt as a catalyst, with or without a solvent.

BRIEF SUMMARY OF THE INVENTION

An exemplary embodiment of a method for preparing the citraconic anhydride includes: providing an itaconic acid as a starting material; and subjecting the itaconic acid to an isomerization/dehydration reaction in the presence of a catalyst to obtain the citraconic anhydride, wherein the catalyst includes a heteropolyacid or heteropolyacid salt.

In another exemplary embodiment of the disclosure, the disclosure also provides a method for isomerizing/dehydrating itaconic acid, including: mixing an itaconic acid with heteropoly acid or salt thereof to form a mixture; and heating the mixture to undergo an isomerization/dehydration reaction, obtaining a citraconic anhydride.

A detailed description is given in the following embodiments with reference to the accompanying drawings.

DETAILED DESCRIPTION OF THE INVENTION

The disclosure provides a method for preparing the citraconic anhydride from itaconic acid with improved yields, suitable for mass industrial production, thus, increasing commercial value of itaconic acid.

The method for preparing the citraconic anhydride of the disclosure employs a heteropolyacid or heteropolyacid salt as a catalyst. Particularly, in the method, the itaconic acid can be converted to citraconic anhydride in the presence or absence of a solvent. Further, after the itaconic acid undergoes isomerization via the heteropolyacid or heteropolyacid salt, a sequential dehydration in a one pot reaction can be conducted on the result, without isolating an intermediate product first.

The method for preparing the citraconic anhydride includes the following steps. An itaconic acid is provided as a starting material. Next, the itaconic acid is subjected to an isomerization/dehydration reaction in the presence of a catalyst to obtain the citraconic anhydride, wherein the catalyst includes a heteropolyacid or heteropolyacid salt.

The heteropolyacid or heteropolyacid salt employed in the disclosure is a solid-acid catalyst. The heteropolyacid is a compound consisting of a center element and peripheral elements to which oxygen is bonded. The center element can include Si, P, Ge, As, B, Ti, Ce, Co, Ni, Al, Ga, Bi, Cr, Sn, or Zr. Specific examples of the peripheral element include metals such as W, Mo, V, or Nb, however, the disclosure is not limited thereto.

These heteropolyacids are known also as a "polyoxoanion", a "polyoxometallic salt" or a "metal oxide cluster". Some structures of well-known anions are named after researchers in the field, for example, Keggin, Wells-Dawson and Anderson-Evans-Perloff structure. These are described in detail in Poly-san no Kagaku, Kikan Kagaku Sosetsu (Chemistry of Polyacids, the Introduction of Chemistry Quarterly), No. 20, compiled by Nippon Kagaku Kai (1993). The heteropolyacid usually has a high molecular weight, for example, a molecular weight of 500 to 9,000, and includes not only a monomer but also a dimeric complex.

The heteropolyacid salt is not particularly limited as below, and can have a chemical structure represented by Formula (I):

$$A_j H_k X M_{12} O_{40} \qquad \text{Formula (I)}$$

wherein, A is independently an alkali metal element, an alkaline earth metal element, an organic amine cation (such $NH_4^+$), or combinations thereof, X is Si, P, Ge, As, B, Ti, Ce, Co, Ni, Al, Ga, Bi, Cr, Sn, or Zr, M is independently Mo, W, V, or Nb, and J is 0-4, k is 0-4, j+K≦4, and at least one of j and k is greater than 0.

Further, the heteropolyacid or heteropolyacid salt can be a compound containing crystallization water, such as $H_4SiW_{12}O_{40} \cdot nH_2O$, $H_3PW_{12}O_{40} \cdot nH_2O$, $H_3PMo_{12}O_{40} \cdot nH_2O$, $H_4SiMo_{12}O_{40} \cdot nH_2O$, $Cs_{2.5}H_{0.5}PW_{12}O_{40} \cdot nH_2O$, or $Cs_4SiW_{12}O_{40} \cdot nH_2O$, wherein n is equal to or great than 0. Specific examples thereof include metal salts such as those of lithium, sodium, potassium, cesium, magnesium, barium, copper, rubidium, thallium, gold and gallium, and onium salts such as ammonia and organic amine, however, the disclosure is not limited thereto. The shape of the substance which can be used as the support for the heteropolyacid or heteropolyacid salt catalyst of the disclosure is not particularly limited and specifically, a powder, spheres, pellets and other optional forms may be used, however, the disclosure is not limited thereto. The support (carrier) of the heteropolyacid or heteropolyacid salt can be an organic or inorganic porous material including mesoporous material, carbon powder, mixed metal oxides, silicon oxide, aluminium oxide, titanium oxide, zirconium oxide, zeolite, or clay. Further, the definition of a heteropolyacid and a heteropolyacid salt is further known as described in U.S. Pat. Nos. 3,998,876, 4,320,227, and 5,191,116.

It should be noted that, in the method for preparing the citraconic anhydride, the isomerization/dehydration reaction can be performed in the presence of the solvent or in the absence of the solvent. In the use of the solvent, the itaconic acid can be first dissolved in the solvent (such as amide, including N-Methyl-2-Pyrrolidone (NMP), or N,N-di-methylacetamide (DMAC) for performing a subsequent isomerization/dehydration reaction. The amide solvent not only promotes the dissolution of itaconic acid and heteropolyacid salt and prevents the itaconic acid from degradation due to uneven heating, but also tends to remove water by forming an azeotrope with water. The weight ratio between the solvent and the itaconic acid can be less than ½. After heating to 130° C., the itaconic acid is completely dissolved in the solvent, and a homogeneous reaction is achieved.

Without the use of the solvent, the itaconic acid can be heated to melt and the itaconic acid is in a melting state when performing the isomerization/dehydration reaction at a reaction temperature of between 160-250° C.

In an embodiment of the disclosure, the water byproduct is removed simultaneously during the dehydration reaction. Particularly, the process for removing water can include reduced pressure distillation or employment of a dehydrating agent. In another embodiment of the disclosure, the water byproduct is not removed during the dehydration reaction.

The dehydrating agent can be aliphatic hydrocarbon compounds (such as octane, isooctane, nonane, decane, undecane, dodecane, or decahydronaphthalene), aromatic hydrocarbon compounds (such as toluene, dimethylbenzene, trimethylbenzene, pseudocumene, tetramethylbenzene, ethylbenzene, diethylbenzene, isopropyl benzene, or paracymene), ether compounds (such as dibutyl ether, isobutyl ether, di(2-ethylhexyl)ether, anisole, ethoxybenzene, diphenyl ether, or ethylene glycol monobutyl ether), ketone compounds (such as butanone, methyl isobutyl ketone, 2,6-dimethyl-4-heptanone, 2-heptanone, or cyclohexanone), or amide compounds (such as Dimethylformamide, dimethyl acetamide, or N-methylpyrrolidinone).

The method for preparing the citraconic anhydride employing heteropolyacid or heteropolyacid salt as the catalyst of the disclosure has following advantages:

(1) Since some of heteropolyacid or heteropolyacid salt has an intrinsic acidity that is stronger than sulfuric acid, the itaconic acid as a starting material dissolved in solvent can be reacted at a relatively low reaction temperature for preparing the citraconic anhydride. For example, the itaconic acid can be completely dissolved in an amide solvent (such as N-Methyl-2-Pyrrolidone) and the isomerization/dehydration reaction can be performed at a temperature of 130° C., achieving a homogeneous reaction. In comparison with conventional processes employing a solvent, the method for preparing the citraconic anhydride of the disclosure has reduced process time and increased yield.

(2) The heteropolyacid or heteropolyacid salt catalyst can be added into a reaction bottle to react with the itaconic acid at a melting state of 160-170° C. After reacting, the crude product can be subjected to reduced pressure distillation (with a pressure of between 50-200 torr) to obtain the citraconic anhydride with a yield of more than 90%.

(3) The method for preparing the citraconic anhydride employing heteropolyacid or heteropolyacid salt as the catalyst of the disclosure can further employ a dehydrating agent (such as a solvent) to remove the water byproduct by azeotropy.

(4) The heteropolyacid or heteropolyacid salt catalyst employed by the method of the disclosure can be recycled easily and reusable. For example, after isolating the citraconic anhydride by distillation, an ester solvent can be added into the residual reaction solution to separate the heteropolyacid or heteropolyacid salt catalyst via sedimentation. To the contrary, the catalyst employed by the conventional methods is apt to react with the itaconic acid or miscible in a residual reaction, and is non-recyclable.

The following examples are intended to illustrate the disclosure more fully without limiting the scope of the disclosure, since numerous modifications and variations will be apparent to those skilled in this art.

EXAMPLE 1

37.9960 g of itaconic acid, 1.0020 g of heteropolyacid $H_3PW_{12}O_{40}$, and 19.0180 g of N-methyl-2-Pyrrolidone were added into a 100 ml reaction bottle. The mixture was heated at 130° C. for 15 min, obtaining a yellow orange clear solution. After reacting for 30 min, reduced pressure distillation was simultaneously performed with aforementioned reaction to remove the water byproduct with a pressure of 150-200 torr. After reacting further for 4 hrs, the yield of the citraconic anhydride was measured by gas chromatography and was 80.51%. The synthesis pathway was as follows:

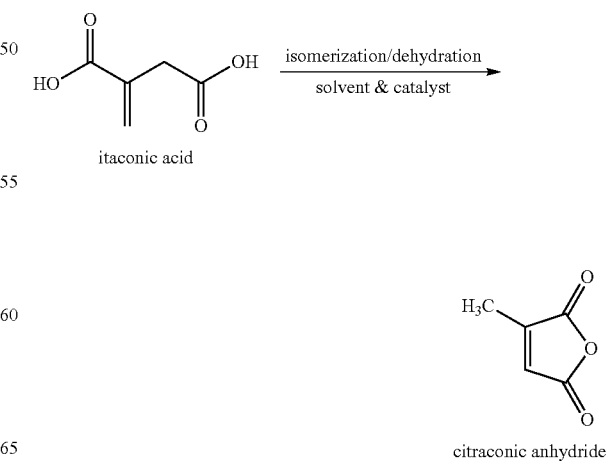

The ratio between reactants and the reaction conditions are shown in Table 1.

EXAMPLE 2

37.986 g of itaconic acid, 1.011 g of heteropolyacid $H_4SiMo_{12}O_{40}$, and 18.996 g of N-methyl-2-Pyrrolidone were added into a 100 ml reaction bottle. The mixture was heated at 130° C. for 15 min, obtaining a yellow orange clear solution. After reacting for 30 min, reduced pressure distillation was simultaneously performed with aforementioned reaction to remove the water byproduct with a pressure of 150-200 torr. After reacting further for 4 hrs, the yield of the citraconic anhydride was measured by gas chromatography and was 81.24%. The ratio between reactants and the reaction conditions are shown in Table 1.

EXAMPLE 3

38.003 g of itaconic acid, 1.004 g of heteropolyacid $H_4SiW_{12}O_{40}$, and 19.008 g of N,N-dimethyl acetamide were added into a 100 ml reaction bottle. The mixture was heated at 130° C. for 15 min, obtaining a yellow orange clear solution. After reacting for 30 min, reduced pressure distillation was simultaneously performed with aforementioned reaction to remove the water byproduct with a pressure of 150-200 torr. After reacting further for 4 hrs, the yield of the citraconic anhydride was measured by gas chromatography and was 71.35%. The ratio between reactants and the reaction conditions are shown in Table 1.

COMPARATIVE EXAMPLE 1

38.156 g of itaconic acid, 1.0066 g of $Na_2SO_4$ (serving as a catalyst), and 14.162 g of N-methyl-2-Pyrrolidone were added into a 100 ml reaction bottle. The mixture was heated at 150° C. for 15 min, obtaining a yellow orange clear solution. After reacting for 30 min, reduced pressure distillation was simultaneously performed with aforementioned reaction to remove the water byproduct with a pressure of 150-200 torr. After reacting further for 4 hrs, the yield of the citraconic anhydride was measured by gas chromatography and was 70.55%. The ratio between reactants and the reaction conditions are shown in Table 1.

TABLE 1

| | solvent | itaconic acid/ solvent (weight ratio %) | catalyst (wt %) (based on the weight of itaconic acid) | reaction temperature (° C.) | yield (%) |
|---|---|---|---|---|---|
| Example 1 | NMP | 2:1 | HPW (2.6 wt %) | 130 | 80.51 |
| Example 2 | NMP | 2:1 | HSiMo (2.6 wt %) | 130 | 81.24 |
| Example 3 | DMAC | 2:1 | HSiW (2.6 wt %) | 130 | 71.35 |
| Comparative Example 1 | NMP | 2.7:1 | $Na_2SO_4$ (2.6 wt %) | 150 | 70.55 |

Remark:
HPW: $H_3PW_{12}O_{40}$;
HSiMo: $H_4SiMO_{12}O_{40}$;
HSiW: $H_4SiW_{12}O_{40}$;
NMP: N-methyl-2-Pyrrolidone; and
DMAC: N,N-dimethyl acetamide.

According to Examples 1-3 and Comparative Example 1, the method for preparing the citraconic anhydride employing solvent of the disclosure can be carried out by a one-pot reaction. The solvent not only promotes the dissolution of itaconic acid and heteropolyacid salt and prevents the itaconic acid from degradation due to uneven heating, but also tends to remove water by forming an azeotrope with water. Due to the acidity of the heteropolyacid, the method for preparing the citraconic anhydride of the disclosure has a high yield advantage. Further, the method can be perform at a relatively low reaction temperature in comparison with convention processes (having a reaction temperature of more than 150° C.).

EXAMPLE 4

100 g of itaconic acid, and 1 g of heteropolyacid $Cs_4SiW_{12}O_{40}$ were mixed and added into a 100 ml reaction bottle without a solvent. The mixture was heated at 190-200° C. for 15 min, and the itaconic acid was at a melting state. After reacting for 30 min, the reaction temperature was reduced to 170° C. and reduced pressure distillation was simultaneously performed with aforementioned reaction to remove the water byproduct with a pressure of 50-100 torr. After reacting further for 5 hrs, the yield of the citraconic anhydride was measured by gas chromatography and was 92.5%. After isolating the citraconic anhydride, 50 ml of ethyl acetate was added into the residual reaction solution to separate the heteropolyacid or heteropolyacid salt catalyst via sedimentation. After filtering, the collected solid was dried to recycle the catalyst $Cs_4SiW_{12}O_{40}$. The ratio between reactants and the reaction conditions are shown in Table 2.

EXAMPLE 5

100 g of itaconic acid, and the heteropolyacid $Cs_4SiW_{12}O_{40}$ recycled from Example 4 were mixed and added into a 100 ml reaction bottle without a solvent. The mixture was heated at 190-200° C. for 15 min, and the itaconic acid was at a melting state. After reacting for 30 min, the reaction temperature was reduced to 170° C. and reduced pressure distillation was simultaneously performed with aforementioned reaction to remove the water byproduct with a pressure of 50-100 torr. After reacting further for 5 hrs, the yield of the citraconic anhydride was measured by gas chromatography and was 92.2%.

The ratio between reactants and the reaction conditions are shown in Table 2.

COMPARATIVE EXAMPLE 2

100 g of itaconic acid, and 1 g of $Na_2SO_4$ (serving as a catalyst) were mixed and added into a 100 ml reaction bottle without a solvent. The mixture was heated at 190-200° C. for 15 min, and the itaconic acid was at a melting state. After reacting for 30 min, the reaction temperature was reduced to 170° C. and reduced pressure distillation was simultaneously performed with aforementioned reaction to remove the water byproduct with a pressure of 50-100 torr. After reacting further for 4 hrs, the yield of the citraconic anhydride was measured by gas chromatography and was 88.9%. The ratio between reactants and the reaction conditions are shown in Table 2.

TABLE 2

| | slovent | catalyst (wt %) (based on the weight of itaconic acid) | reaction temperature (° C.) | yield (%) |
|---|---|---|---|---|
| Example 4 | non-solvent | CsSiW (1 wt %) | 170 | 92.5 |
| Example 5 | non-solvent | CsSiW (recycled from Example 4) | 170 | 92.2 |
| Comparative Example 2 | non-solvent | Na$_2$SO$_4$ (1 wt %) | 170 | 88.9 |

Remark:
CsSiW: Cs$_4$SiW$_{12}$O$_{40}$.

According to Examples 4-5 and Comparative Example 2, the method for preparing the citraconic anhydride in the absence the solvent can also be carried out by a one-pot reaction. The heteropolyacid or heteropolyacid salt catalyst can be recycled, and the reaction employing the recycled catalyst has a great citraconic anhydride manufacturing yield.

EXAMPLE 6

50.006 g of itaconic acid, 1.006 g of Na$_4$SiW$_{12}$O$_{40}$, and 50.009 g of pseudocumene were mixed and added into a 100 ml reaction bottle. The mixture was heated at 190° C. to remove the water byproduct by azeotropy. After completely removing the water byproduct, the citraconic anhydride was purified by distillation with a pressure of 50-100 torr. The yield of the citraconic anhydride was measured by gas chromatography and was 84.4%.

EXAMPLE 7

50.004 g of itaconic acid, 1.011 g of K$_4$SiW$_{12}$O$_{40}$, and 50.007 g of ortho xylene were mixed and added into a 100 ml reaction bottle. The mixture was heated at 190° C. to remove the water byproduct by azeotropy. After completely removing the water byproduct, the citraconic anhydride was purified by distillation with a pressure of 50-100 torr. The yield of the citraconic anhydride was measured by gas chromatography and was 73.8%.

TABLE 3

| | dehydrating agent (solvent) | catalyst (wt %) (based on the weight of itaconic acid) | reaction temperature (° C.) | yield (%) |
|---|---|---|---|---|
| Example 6 | pseudocumene | NaSiW (2 wt %) | 170 | 84.40 |
| Example 7 | orthoxylene | KSiW (2 wt %) | 170 | 73.80 |

Remark:
NaSiW: Na$_4$SiW$_{12}$O$_{40}$; and
KSiW: K$_4$SiW$_{12}$O$_{40}$.

According to Examples 6-7, the method for preparing the citraconic anhydride can further employ a dehydrating agent for removing water byproduct by azeotropy, and the product can be purified by distillation with a high yield.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for preparing the citraconic anhydride, comprising:
    providing an itaconic acid as a starting material; and
    subjecting the itaconic acid to an isomerization/dehydration reaction in the presence of a catalyst to obtain the citraconic anhydride, wherein the catalyst comprises a heteropolyacid or heteropolyacid salt.

2. The method as claimed in claim 1, wherein the itaconic acid is in a melting state when subjected to the isomerization/dehydration reaction.

3. The method as claimed in claim 1, wherein the itaconic acid is dissolved in a solvent.

4. The method as claimed in claim 3, wherein the solvent comprises a polar solvent or non-polar solvent.

5. The method as claimed in claim 1, further comprising:
    removing a water byproduct during the dehydration reaction.

6. The method as claimed in claim 5, wherein the process for removing water comprises reduced pressure distillation.

7. The method as claimed in claim 5, wherein the process for removing water employs a dehydrating agent.

8. The method as claimed in claim 1, wherein a water byproduct is not removed during the dehydration reaction.

9. The method as claimed in claim 3, wherein the solvent is capable of forming an azeotrope with water.

10. The method as claimed in claim 1, wherein the heteropolyacid or heteropolyacid salt has a chemical structure represented by Formula (I)

$$A_jH_kXM_{12}O_{40} \quad \text{Formula (I)}$$

wherein, A is independently an alkali metal element, an alkaline earth metal element, an organic amine cation, or combinations thereof,
X is Si, P, Ge, As, B, Ti, Ce, Co, Ni, Al, Ga, Bi, Cr, Sn, or Zr,
M is independently Mo, W, V, or Nb, and
J is 0-4, k is 0-4, j+K≦4, and at least one of j and k is greater than 0.

11. The method as claimed in claim 1, wherein the heteropolyacid or heteropolyacid salt is a compound containing crystallization water.

12. The method as claimed in claim 1, wherein the heteropolyacid or heteropolyacid salt comprises H$_4$SiW$_{12}$O$_{40}$ · nH$_2$O, H$_3$PW$_{12}$O$_{40}$ · nH$_2$O, H$_3$PMo$_{12}$O$_{40}$ · nH$_2$O, H$_4$SiMo$_{12}$O$_{40}$ · nH$_2$O, Cs$_{2.5}$H$_{0.5}$PW$_{12}$O$_{40}$ · nH$_2$O, or Cs$_4$SiW$_{12}$O$_{40}$ · nH$_2$O, and n is equal to or great than 0.

13. The method as claimed in claim 1, wherein the heteropolyacid or heteropolyacid salt is supported on a carrier, and the carrier is an organic or inorganic porous material comprising mesoporous material, carbon powder, mixed metal oxides, silicon oxide, aluminium oxide, titanium oxide, zirconium oxide, zeolite, or clay.

14. A method for isomerizing/dehydrating itaconic acid, comprising:
    mixing an itaconic acid with heteropoly acid or salt thereof to form a mixture; and
    heating the mixture to undergo an isomerization/dehydration reaction, obtaining a citraconic anhydride.

15. The method as claimed in claim 14, wherein the itaconic acid is in a melting state when subjected to the isomerization/dehydration reaction.

16. The method as claimed in claim 14, wherein the itaconic acid is dissolved in a solvent when subjected to the isomerization/dehydration reaction.

17. The method as claimed in claim 14, further comprising: removing a water byproduct during the dehydration reaction via reduced pressure distillation.

18. The method as claimed in claim 14, further comprising: removing a water byproduct during the dehydration reaction by adding a dehydrating agent.

19. The method as claimed in claim 16, wherein the solvent is capable of forming an azeotrope with water.

* * * * *